(12) United States Patent
Sanganabhatla et al.

(10) Patent No.: US 8,450,376 B2
(45) Date of Patent: May 28, 2013

(54) AMORPHOUS BUPROPION HYDROBROMIDE AND PREPARATION THEREOF

(75) Inventors: Shankar Sanganabhatla, Navi Mumbai (IN); Vijay Soni, Suffern, NY (US); Mubeen Ahmed Khan, Navi Mumbai (IN); Nandlal Agarwal, Bharuch (IN); Hemanth Kamble, Mumbai (IN); Sharad Gore, Thane (IN)

(73) Assignee: Glenmark Generics Ltd., Chakala, Andheri (East), Mumbai (IN)

( * ) Notice: Subject to any disclaimer, the term of this patent is extended or adjusted under 35 U.S.C. 154(b) by 266 days.

(21) Appl. No.: 12/997,881

(22) PCT Filed: Jun. 15, 2009

(86) PCT No.: PCT/IB2009/005936
§ 371 (c)(1),
(2), (4) Date: Dec. 14, 2010

(87) PCT Pub. No.: WO2010/004386
PCT Pub. Date: Jan. 14, 2010

(65) Prior Publication Data
US 2011/0105619 A1     May 5, 2011

Related U.S. Application Data

(60) Provisional application No. 61/134,275, filed on Jul. 8, 2008.

(30) Foreign Application Priority Data

Jun. 16, 2008    (IN) .......................... 1266/MUM/2008

(51) Int. Cl.
*A61K 31/12*      (2006.01)
*A61K 31/137*     (2006.01)
*C07C 225/16*    (2006.01)

(52) U.S. Cl.
USPC ............ 514/649; 564/342; 564/343; 564/345

(58) Field of Classification Search
None
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 5,763,493 A | 6/1998 | Ruff et al. |
| 6,306,436 B1 | 10/2001 | Chungi et al. |
| 6,462,237 B1 | 10/2002 | Gidwani et al. |
| 2007/0281012 A1 | 12/2007 | Oberegger et al. |
| 2008/0038348 A1 | 2/2008 | Oberegger et al. |
| 2008/0051606 A1 | 2/2008 | Oberegger et al. |

*Primary Examiner* — Brian J Davis
(74) *Attorney, Agent, or Firm* — MariaLouisa Lao

(57) ABSTRACT

The present invention provides an amorphous bupropion hydrobromide and an amorphous bupropion hydrobromide granulates with at least one pharmaceutically acceptable carrier, and a process for its preparation.

4 Claims, 3 Drawing Sheets

Glenmark Generics Limited

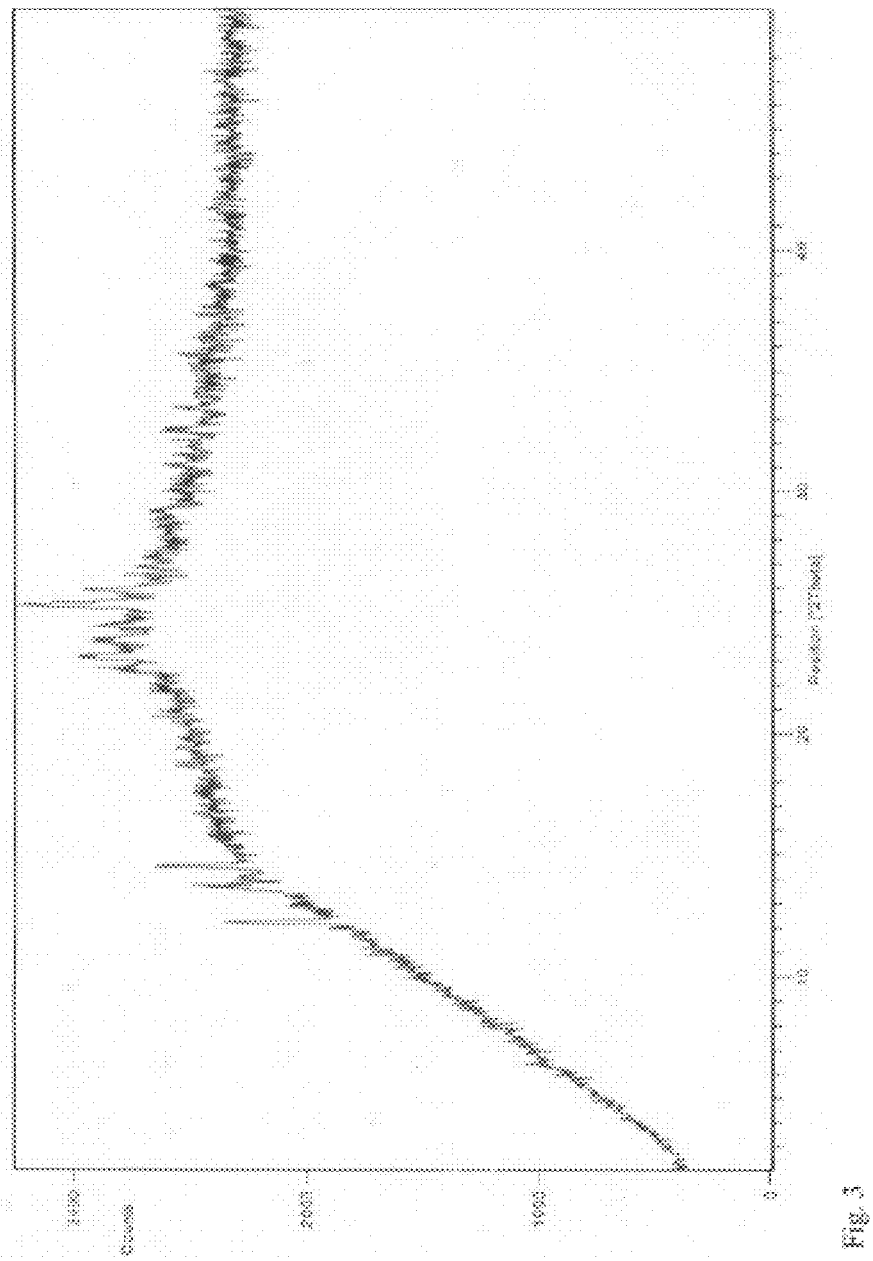

AMORPHOUS BUPROPION HYDROBROMIDE AND PREPARATION THEREOF

PRIORITY

This application is a 35 U.S.C. 371 National Stage Filing of International Application No. PCT/IB2009/005936, filed Jun. 15, 2009. This application claims the benefit under 35 U.S.C. §119 to U.S. provisional application No. 61/134,275 filed on Jul. 8, 2008 and to Indian Provisional Application No. 1266/MUM/2008 filed on Jun. 16, 2008, the contents of each of which are incorporated by reference herein.

BACKGROUND OF THE INVENTION

1. Technical Field

The present invention generally relates to an amorphous bupropion hydrobromide, processes for preparation thereof, and stable pharmaceutical compositions therewith.

The present invention also provides an amorphous bupropion hydrobromide granulate with al least one pharmaceutically acceptable carrier, processes for preparation thereof, and stable pharmaceutical compositions therewith.

2. Description of the Related Art

Bupropion is an antidepressant agent that is chemically distinct from tricyclic, tetracyclic and other commercially available antidepressants, e.g., selective serotonin-reuptake inhibitors, or "SSRIs." m-chloro-α-(t-butylamino) propiophenone (herein "Bupropion") has a CAS No. of 34911-55-2, described in U.S. Pat. Nos. 3,819,706 and 3,885,046, and is represented by the structure of Formula I:

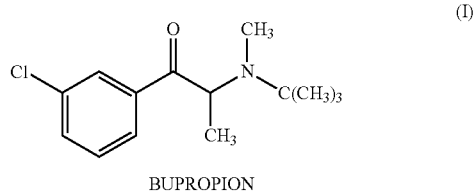 [SMILES: CC(C(=O)c1cccc(Cl)c1)N(C)C(C)(C)C]

BUPROPION (I)

Bupropion is the free base form of bupropion hydrobromide, which has a CAS number of 905818-69-1 and the following structure:

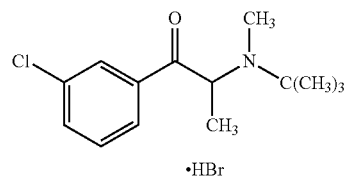 [SMILES: CC(C(=O)c1cccc(Cl)c1)N(C)C(C)(C)C ; Br]

Bupropion hydrobromide was approved by the USFDA under the name APLENZIN® in the form of 174, 348, 522 mg tablets and is indicated for the treatment of major depressive disorder.

US Publication No. 2008051606 discloses three different crystalline polymorphic forms of bupropion hydrobromide named as Form-I, II, and III and can be characterized by powder X-ray powder diffraction pattern (PXRD).

The discovery of new amorphous forms of active pharmaceutical ingredients ("APIs") provides opportunities to improve the performance characteristics, the solubility, stability, flowability, tractability and compressibility of drug substances and the safety and efficacy of drug products of a pharmaceutical product. Such discoveries enlarge the repertoire of materials that a formulation scientist has available for designing, for example, a pharmaceutical dosage form of a drug with a targeted release profile or other desired characteristic.

Generally, amorphous solids offer opportunities for solubility and bioavailability enhancement since these materials are more soluble than the crystalline form of the same compound. The rate of dissolution is also a consideration in formulating syrups, elixirs and other liquid medicaments.

Hence, it is desirable to provide methods of producing bupropion hydrobromide exhibiting enhanced bioavailability compared to the crystalline form of the compound. By converting a substantial portion of crystalline bupropion hydrobromide to the amorphous state, the aqueous solubility and bioavailability are increased. Furthermore, bupropion hydrobromide presented as an amorphous solid may facilitate manufacturing of both the active ingredient and the finished product and enable the use of reduced size dosage forms. Moreover, the selective customization of the properties of particles comprising bupropion hydrobromide can offer intriguing opportunities for pharmaceutical production and drug delivery. The morphology of individual particles plays a central role in this pursuit, since morphology directly influences bulk powder properties, such as density, residual solvent content, and flowability. In addition, techniques that modify particle shape and interior structure may profoundly affect pharmacokinetic properties, such as drug release rate, solubility, and bioavailability. Thus, the ability to design particle morphology has significant implications for the production process and product attributes.

SUMMARY OF THE INVENTION

The present invention provides an amorphous bupropion hydrobromide.

The present invention provides an amorphous bupropion hydrobromide granulate with at least one pharmaceutically acceptable carrier.

The present invention provides an amorphous bupropion hydrobromide granulate with at least one pharmaceutically acceptable carrier, wherein the granulate is in form of a solid dispersion, an inclusion complex, or a spray granulate.

The present invention provides an amorphous bupropion hydrobromide granulate with at least one pharmaceutically acceptable carrier; wherein the pharmaceutically acceptable carrier comprises one or more of a povidone, meglumine, gum, ethyl cellulose, hydroxypropyl cellulose, hydroxypropyl methyl cellulose, hydroxypropyl ethyl cellulose, microcrystalline cellulose, cyclodextrin, gelatin, hypromellose phthalate, lactose, polyhydric alcohol, polyethylene glycol, polyethylene oxide, polyoxyalkylene derivative, methacrylic acid copolymer, polyvinyl alcohol, propylene glycol derivative, fatty acid, fatty alcohols, or esters of fatty acids.

The present invention provides a process for preparation of an amorphous bupropion hydrobromide, which includes:

a) providing:
  i) a solution or mixture of bupropion hydrobromide and at least one pharmaceutically acceptable carrier in a solvent; or
  ii) a mixture or a solution of bupropion, hydrobromic acid, and at least one pharmaceutically acceptable carrier in a solvent;

b) isolating the amorphous bupropion hydrobromide from the solution; and c) optionally, drying the amorphous bupropion hydrobromide.

The present invention provides a pharmaceutical composition comprising an amorphous bupropion hydrobromide.

The present invention provides a pharmaceutical composition comprising an amorphous bupropion hydrobromide granulate with at least one pharmaceutically acceptable carrier.

The present invention provides use of an amorphous bupropion hydrobromide for the preparation of a pharmaceutical composition for use in the treatment of depressive disorders or smoking cessation.

The present invention provides use of an amorphous bupropion hydrobromide granulate with at least one pharmaceutically acceptable carrier for the preparation of a pharmaceutical composition for use in the treatment of or smoking cessation

BRIEF DESCRIPTION OF THE DRAWINGS

FIG. 3: X-ray diffraction (XRPD) pattern of amorphous bupropion hydrobromide, prepared as in Example 3.

DETAILED DESCRIPTION OF THE INVENTION

Figure 1:
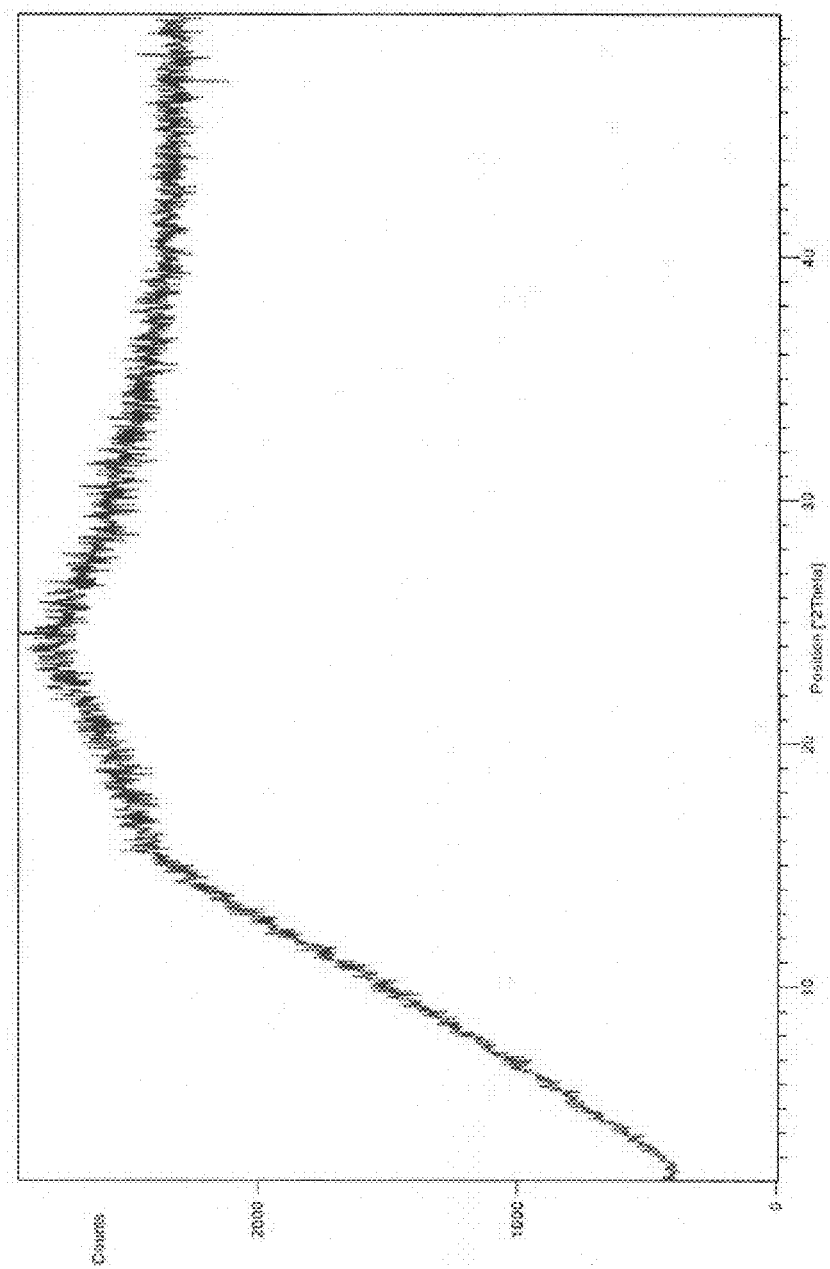
FIG. 1: X-ray diffraction (XRPD) pattern of a bupropion hydrobromide solid dispersion with (2-hydroxy propyl)-β-cyclodextrin, prepared as in Example 1.

The crystallinity of the chemical compounds is established using powder X-ray diffraction pattern (XRPD). Crystalline peaks produced by an X-ray diffraction measurement, are characterized by having a half-value width below 2 degrees. Amorphous solids, in contrast to crystalline forms, do not possess a distinguishable crystal lattice and do not have an orderly arrangement of structural units so that amorphous solids are not giving a definitive X-ray diffraction pattern. They also do not give rise to a melting point and tend to liquefy at some point beyond the glass transition point. Amorphous forms are generally more soluble, and thus they are desirable for pharmaceutical purposes because the bioavailability of amorphous compounds may be greater than their crystalline counterparts.

The present invention provides novel amorphous bupropion hydrobromide and amorphous bupropion hydrobromide granulate with at least one pharmaceutically acceptable carrier, processes for preparation thereof, and stable pharmaceutical compositions therewith.

The present invention provides novel amorphous bupropion hydrobromide; particularly amorphous bupropion hydrobromide granulate together with at least one pharmaceutically acceptable carrier; wherein the granulate is in form of a solid dispersion, an inclusion complex, or a spray granulate.

We have found that the stability of amorphous bupropion hydrobromide is increased by including bupropion hydrobromide in the inner cavity of at least one pharmaceutically acceptable carrier, where they are protected from external influences.

The pharmaceutically acceptable carriers includes but are not limited to hydrophilic carriers such as polymers of N-vinylpyrrolidone commonly known as polyvinylpyrrolidine, "PVP," or "povidone", meglumine, gum, cellulose derivatives such as microcrystalline cellulose (MCC), methyl cellulose, ethyl cellulose, hydroxypropyl cellulose (HPC or hypromellose), hydroxypropyl methylcellulose(HPMC), hydroxypropyl ethyl cellulose (HPEC), cyclodextrins, gelatin, hypromellose phthalate, lactose, polyhydric alcohols, polyethylene glycols (PEG), polyethylene oxides, polyoxyalkylene derivatives, methacrylic acid copolymers, polyvinyl alcohols, and propylene glycol derivatives, fatty acids, fatty alcohols, or esters of fatty acids; or its derivatives thereof.

Useful pyrrolidones include, but are not limited to homopolymers or copolymers of N-vinylpyrrolidone. Such polymers can form complexes with a variety of compounds. The water-soluble forms of N-vinylpyrrolidone are available in a variety of viscosity and molecular weight grades such as but not limited to PVP K-12, PVP K-15, PVP K-17, PVP K-25, PVP K-30, PVP K-90, PVP K-120 and crospovidone.

Polyethylene glycols, condensation polymers of ethylene oxide and water, are commercially available from various manufacturers in average molecular weights ranging from about 300 to about 10,000,000 Daltons. Some of the grades that are useful in the present invention include, but are not limited to, PEG 1500, PEG 4000, PEG 6000, PEG 8000, etc.

Among various cyclodextrins α-, β-, γ- and ε-cyclodextrins or their methylated or hydroxyalkylated derivatives may be used. Methods for preparation of the granulates are described below. Similar preparative process can be used irrespective of whether α-, β-, γ- and ε-cyclodextrins, or their methylated or hydroxyalkylated derivates are used.

Any pharmaceutical carrier will be acceptable as long as it allows the formation of the stable amorphous granulate of bupropion hydrobromide as described herein, is compatible with the bupropion hydrobromide, and is acceptable for human pharmaceutical use. The choice of carrier is within the scope of understanding of a person skilled in the art and is not limited by the list of carriers above.

Preferably the pharmaceutically acceptable carriers are a povidone, cyclodextrins, lactose, hydroxypropyl methyl cellulose, ethyl cellulose, or polyethylene glycol; more preferably the pharmaceutically acceptable carriers are povidone, (2-hydroxy propyl)-(3-cyclodextrin, lactose, or hydroxypropyl methyl cellulose.

The present invention provides a process for preparation of an amorphous bupropion hydrobromide; comprising:

a) providing:
  i) a solution or mixture of bupropion hydrobromide and at least one pharmaceutically acceptable carrier in a solvent; or
  ii) a mixture or a solution of bupropion, hydrobromic acid, and at least one pharmaceutically acceptable carrier in a solvent;

b) isolating the amorphous bupropion hydrobromide from the solution; and c) optionally, drying the amorphous bupropion hydrobromide.

The first step of providing a solution of bupropion hydrobromide or a solution of bupropion, hydrobromic acid for the preparation of the amorphous bupropion hydrobromide according to the invention involves mixing at least one pharmaceutically acceptable carrier as described herein above with a suitable solvent. The solution is then stirred until the desired form of bupropion hydrobromide is formed. The solution is then isolated and dried afterwards in an appropriate manner.

Suitable solvents that may be used for providing a solution of bupropion hydrobromide together with at least one pharmaceutically acceptable carrier include but are not limited to polar and non-polar solvents, and mixtures thereof. Nonlimiting examples of polar solvents include, but are not limited to water, methanol, ethanol, n-propanol, isopropanol, n-butanol, isobutanol, t-butanol, 1,4-dioxane, tetrahydrofuran, acetone, acetonitrile, dimethylsulfoxide (DMSO), N-methyl pyrrolidone (NMP), N,N-dimethylformamide (DMF) and N,N-dimethylacetamide (DMAc); non-polar solvents include, but are not limited to n-hexane, benzene, toluene, diethyl ether, chloroform, ethyl acetate, dichloromethane; and mixtures thereof. Preferably the Suitable solvents for providing a solution of bupropion hydrobromide together with one or more pharmaceutically acceptable carriers are water, methanol, ethanol, dichloromethane, dimethylsulfoxide, N,N-dimethylformamide; more preferably the suitable solvent is water, ethanol, or dichloromethane.

The ratio between the bupropion and the pharmaceutically acceptable carrier is not critical and usually depends on the desired final dose of bupropion in tablets or capsules. Preferably the bupropion hydrobromide and a pharmaceutically acceptable carrier are present in a molar ratio of 1:(0.001-4); more preferably the bupropion hydrobromide and a pharmaceutically acceptable carrier are present in a molar ratio of 1:(0.01-2).

The pharmaceutically acceptable carrier that are used for the preparation of the amorphous bupropion hydrobromide of the present invention may optionally be pretreated with reagents such as sodium metabisulfite, sodium sulfite, butylated hydroxytoluene, trialkyl amine, aldehydes, alkali or alkaline earth metal hydroxides like sodium hydroxide, potassium hydroxide, dimethylsulfoxide, and the like, in order to remove any contaminants that may cause undesired impurity formation during the preparation of the amorphous bupropion hydrobromide, which in turn may result in a amorphous bupropion hydrobromide contaminated with undesired impurities for a pharmaceutical product.

The dissolution temperature for the bupropion hydrobromide, optionally along with at least one pharmaceutically acceptable carrier, may range from about 0° C. to about 130° C., or the reflux temperature of the solvent used. Any other temperatures may also be acceptable, provided a clear solution of the concerned materials is obtained in the solvents chosen, and the starting materials are not degraded. It will be understood that the temperatures required will also be determined by the processing conditions for the recovery of the final product, such as the temperature of drying, the boiling point of the solvent, the homogeneity of the solution required after mixing solvents, the viscosity of the solution, the stability of the bupropion hydrobromide and the pharmaceutically acceptable carrier. Such variations are all included herein without any limitation.

The isolation of the resultant product is accomplished by removal of solvent from the solution by, for example, substantially complete evaporation of the solvent, concentrating the solution, cooling to obtain amorphous form and filtering the solid under inert atmosphere. Alternatively, the solvent may also be removed by evaporation. Evaporation can be achieved at sub-zero temperatures by the lyophilisation or freeze-drying technique, a rotational drying (such as with the Buchi Rotavapor), spray drying, fluid bed drying, flash drying, spin flash drying and thin-film drying.

One of the preferred methodologies to remove the solvent involves lyophilisation, in which a solution of bupropion hydrobromide and at least one pharmaceutically acceptable carrier is frozen in a cooling step that is typically over a period of about 30 min to 10 hours, preferably about 1 hours to about 5 hours, more preferably about 2 hours to about 4 hours to result in a frozen mass. A quick freezing generally favors amorphous product, while a slow cooling generally favors a more crystalline product; however, this is only a general guideline, and particular results can vary depending on a number of conditions.

Once frozen, the mass is subjected to a vacuum pressure whereby a substantial portion of the solvent is volatilized off during primary drying. Remaining residual amounts removed in a secondary drying step. Generally, during the primary drying the product temperature is maintained below 0° C. while in the secondary drying the product temperature will be maintained at about 25° C. to about 40° C., although other primary and secondary drying temperatures may be suitably found in the ordinary course by those of ordinary skill in the art.

Another preferred methodologies to remove the solvent involves spray-drying, in which a solution of bupropion hydrobromide and at least one pharmaceutically acceptable carrier is sprayed into the spray drier at the flow rate ranging from 10 to 300 ml/hr, preferably flow rate is 40 to 200 ml/hr. The air inlet temperature to the spray drier used may range from 25 to 200° C. and preferably from 25° C. to 150° C. An "inlet temperature" is the temperature at which the solution enters the spray dryer.

The outlet air temperature used may range from 5° C. to 100° C., preferably outlet temperature is from about 5° C. to about 60° C., and most preferably outlet temperature is from about 5° C. to about 45° C. An "outlet temperature" is the temperature at which the gas exits the spray dryer.

The amorphous bupropion hydrobromide recovered using the process of the present invention is in form of an amorphous bupropion hydrobromide granulates with at least one pharmaceutically acceptable carrier.

The bupropion hydrobromide granulate with at least one pharmaceutically acceptable carrier is stable during storage. This property is important and advantageous for the desired use of bupropion hydrobromide in pharmaceutical product formulations.

Individual particles of the original components are not distinguishable in the granulates, using techniques such as optical microscopy. While the invention is not to be bound to any particular theory, the granulates in some instances can be considered to be granulates at a molecular level, or solid solutions.

The bupropion hydrobromide granulates with at least one pharmaceutically acceptable carrier of the present invention are in substantially amorphous state, can be characterized by an X-ray powder diffraction (XRPD) pattern.

The processes described herein may include drying of the product with or without vacuum and in the presence or absence of an inert atmosphere. Other conventional drying methods may also be used.

The amorphous bupropion hydrobromide granulates of the present invention have commercially acceptable pharmacokinetic characteristics, solubility, flow properties, stability, and the like. The products may optionally be milled to get the desired particle size distributions. Milling or micronization may be performed prior to drying, or after the completion of drying of the products. The milling operation reduces the size of particles and increases surface area of particles by colliding particles with each other at high velocities.

The present invention provides characterization of an amorphous bupropion hydrobromide; particularly amorphous bupropion hydrobromide granulates with at least one pharmaceutically acceptable carrier via X-ray powder diffraction pattern and/or melting point. The X-Ray powder diffraction pattern can be measured by an X-ray powder Diffractometer equipped with a Cu-anode ($\lambda$=1.54 Angstrom), X-ray source operated at 45 kV, 40 mA and a Ni filter is used to strip K-beta radiation. Two-theta calibration is performed using an NIST SRM 640c Si standard. The sample was analyzed using the following instrument parameters: measuring range=2-50° 2θ; step width=0.017°; and measuring time per step=5 sec.

The powder X-ray diffraction pattern of the amorphous bupropion hydrobromide granulates with at least one pharmaceutically acceptable carrier shows no characteristic peaks, thereby identifying that the amorphous structure is present.

The present invention further provides an amorphous bupropion hydrobromide, particularly an amorphous bupropion hydrobromide granulates with at least one pharmaceutically acceptable carrier, having a chemical purity of 98% or more as measure by HPLC, preferably 99% or more, more preferably 99.8% or more. Moreover, the amorphous bupropion hydrobromide, particularly an amorphous bupropion hydrobromide granulates with at least one pharmaceutically acceptable carrier may be obtained substantially free of any unknown impurity, e.g., a content of less than about 0.1% of impurities.

The present invention also encompasses a pharmaceutical composition comprising a therapeutically effective amount of an amorphous bupropion hydrobromide; particularly an amorphous bupropion hydrobromide granulates with at least one pharmaceutically acceptable carrier or other excipients.

The present invention further provides, when a pharmaceutical composition comprising amorphous bupropion hydrobromide prepared according to the present invention is formulated for oral administration or parenteral administration. Accordingly, $D_{50}$ and $D_{90}$ particle size of the unformulated amorphous bupropion hydrobromide of the present invention used as starting material in preparing a pharmaceutical composition generally is less than 300 microns preferably less than about 200 microns, more preferably less than 150 microns, still more preferably less than about 50 microns and still more preferably less than about 10 microns.

Any milling, grinding, micronizing or other particle size reduction method known in the art can be used to bring the solid state amorphous bupropion hydrobromide of the present invention into any desired particle size range as set forth above.

Amorphous bupropion hydrbromide described in the present invention may be formulated into solid pharmaceutical products for oral administration in the form of capsules, tablets, pills, powders or granules. In these compositions, the active ingredient is combined with one or more pharmaceutically acceptable excipients. The drug substance also may be formulated into liquid compositions for oral administration including for example solutions, suspensions, syrups, elixirs and emulsions, containing solvents or vehicles such as water, sorbitol, glycerine, propylene glycol or liquid paraffins.

Compositions for parenteral administration may be suspensions, emulsions or aqueous or non-aqueous, sterile solutions. As a solvent or vehicle, propylene glycol, polyethylene glycol, vegetable oils, olive oil, and injectable organic esters, e.g. ethyl oleate, may be employed.

Suitable pharmaceutical compositions are solid dosage forms, such as tablets with immediate release or sustained release of the active principle, effervescent tablets or dispersion tablets and capsules.

Optionally, the pharmaceutical compositions of the invention may be combination products comprising one or more additional pharmaceutically active components in addition to bupropion.

Pharmaceutically acceptable excipients include, but are not limited to, diluents such as starch, pregelatinized starch, lactose, powdered cellulose, microcrystalline cellulose, dicalcium phosphate, tricalcium phosphate, mannitol, sorbitol and sugar; binders such as acacia, guar gum, tragacanth, gelatin, polyvinylpyrrolidones, hydroxypropyl celluloses, hydroxypropylmethyl celluloses and pregelatinized starch; disintegrants such as starch, sodium starch glycolate, pregelatinized starch, crospovidones, croscarmellose sodium and colloidal silicon dioxide; lubricants such as stearic acid, talc, magnesium stearate and zinc stearate; glidants such as colloidal silicon dioxide; solubility or wetting enhancers such as anionic or cationic or neutral surfactants, complex forming agents such as various grades of cyclodextrins and resins; release rate controlling agents such as hydroxypropyl celluloses, hydroxymethyl celluloses, hydroxypropyl methylcelluloses, ethyl celluloses, methyl celluloses, various grades of methyl methacrylates, and waxes. Other pharmaceutically acceptable excipients that are of use include but are not limited to film formers, film coating agents, plasticizers, colorants, flavoring agents, sweeteners, viscosity enhancers, preservatives, and antioxidants.

Unless defined otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described.

Unless stated to the contrary, any use of the words such as "including," "containing," "comprising," "having" and the like, means "including without limitation" and shall not be construed to limit any general statement that it follows to the specific or similar items or matters immediately following it. Embodiments of the invention are not mutually exclusive, but may be implemented in various combinations.

For purposes of the present invention, the following terms are defined below.

The term "composition" includes, but is not limited to, a powder, a suspension, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, additional active ingredient(s), and pharmaceutically acceptable excipients.

The term "excipient" means a component of a pharmaceutical product that is not the active ingredient, such as filler, diluent, carrier, and so on. The excipients that are useful in preparing a pharmaceutical composition are preferably generally safe, non-toxic and neither biologically nor otherwise undesirable, and are acceptable for veterinary use as; well as human pharmaceutical use. "A pharmaceutically acceptable excipient" as used in the specification and claims includes both one and more than one such excipient.

The term, "solid dispersion", used herein is intended to mean that bupropion hydrobromide is embedded or dispersed or encompassed with in the matrix of pharmaceutically acceptable carrier.

The term, "an inclusion complex", used herein is intended to mean that bupropion hydrobromide is included in the inner cavity of the pharmaceutically acceptable carrier.

The term, "spray granulate", used herein is intended to mean that bupropion hydrobromide is embedded or dispersed or encompassed with in the matrix of pharmaceutically acceptable carrier by spray granulation method.

The term, "isolating" used herein is intended to mean that a chemical state well known among pharmaceutical chemists wherein the recited pharmaceutical ingredient has been separated from the medium in which it was created into a relatively pure physical state, before it is mixed with other pharmaceutical ingredients.

The following examples are provided to enable one skilled in the art to practice the invention and are merely illustrative of the invention. The examples should not be read as limiting the scope of the invention as defined in the features and advantages.

EXAMPLES

Example 1

Preparation of Amorphous Bupropion Hydrobromide Solid Dispersion with (2-Hydroxy Propyl)-β-Cyclodextrin 2.0 gms of bupropion hydrobromide dissolved in 20 ml of water and then with stirring 0.1 gm of (2-Hydroxy propyl)-β-cyclodextrin is added. The mixture is stirred at 50° C. until most of material is dissolved. The resultant solution is filtered through a sterile 0.2 μm filter directly into a lyophilization flask, frozen and lyophilized.
Yield: 1.85 gms
XRD: As set forth in FIG. 1

Example 2

Figure 2:
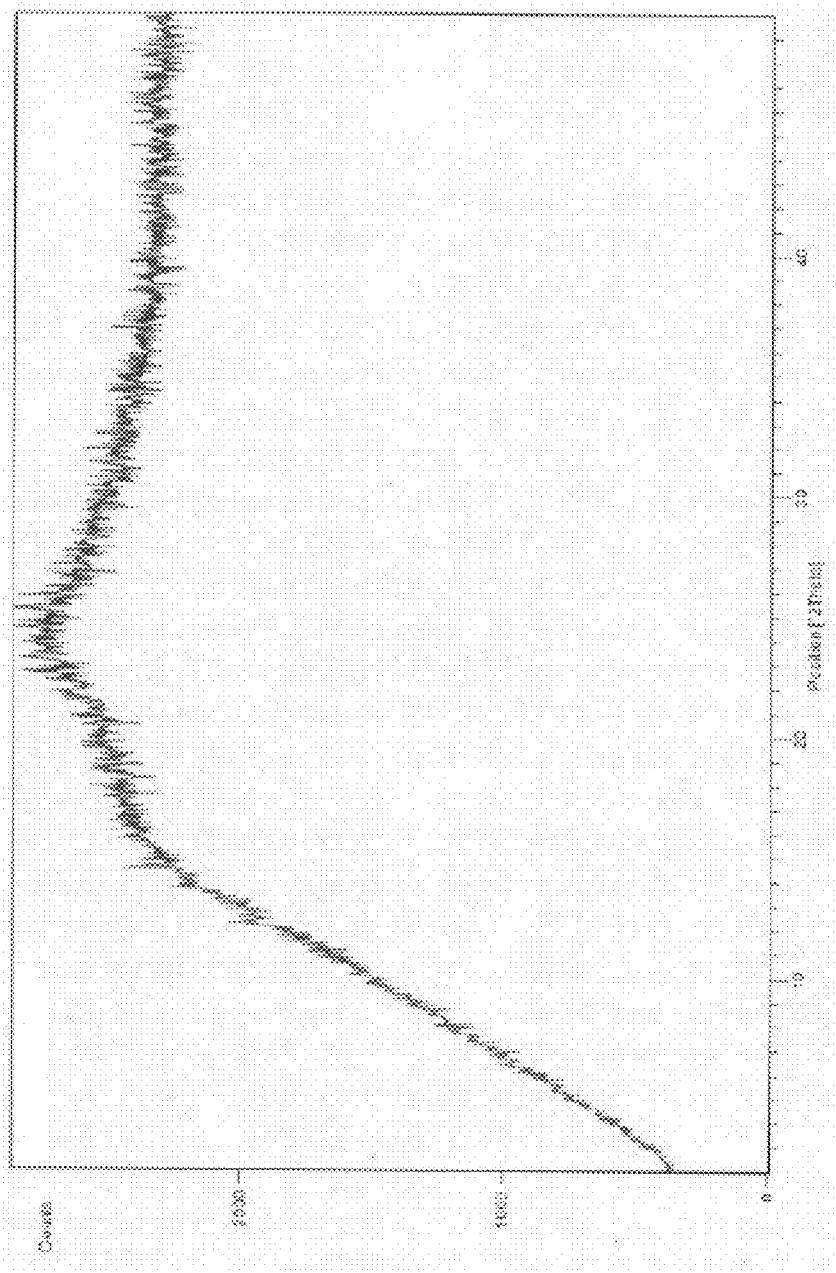
FIG. 2: X-ray diffraction (XRPD) pattern of a bupropion hydrobromide solid dispersion with lactose monohydrate pharmatose, prepared as in Example 2.

Preparation of Amorphous Bupropion Hydrobromide Solid Dispersion with Lactose Monohydrate Pharmatose 2.0 gms of bupropion hydrobromide dissolved in 20 ml of water and then with stirring 0.1 gm of lactose monohydrate pharmatose is added. The mixture is stirred at 50° C. until most of material is dissolved. The resultant solution is filtered through a sterile 0.2 μm filter directly into a lyophilization flask, frozen and lyophilized.
Yield: 1.85 gms
XRD: As set forth in FIG. 2

Example 3

Preparation of Amorphous Bupropion Hydrobromide 2.0 gms of bupropion hydrobromide dissolved in 20 ml of water. The resultant solution is filtered through a sterile 0.2 μm filter directly into a lyophilization flask, frozen and lyophilized.
Yield: 1.8 gms
XRD: As set forth in FIG. 3

Example 4

Preparation of Amorphous Bupropion Hydrobromide Solid Dispersion with β-Cyclodextrin 10 gms of bupropion hydrobromide dissolved in 100 ml of water and then with stirring 0.5 gm of β-cyclodextrin is added. The resultant solution is filtered through a sterile 0.2 μm filter directly into a lyophilization flask, frozen and lyophilized.
Yield: 9.5 gms Example 5

Preparation of an Amorphous Bupropion Hydrobromide Granulates with Povidone K25

2.0 gms of bupropion hydrobromide, 0.5 gms of povidone K25, and 0.5 gms of meglumine are dissolved in 20 ml of water. The resultant solution is filtered through a sterile 0.2 μm filter and sprayed in to a spray dryer followed by dried to give the title compound.

The resulting amorphous spray-dried granulate further compressed into tablets or filled in capsules.

Example 6

Preparation of an Amorphous Bupropion Hydrobromide Solid Dispersion with Hydroxylpropyl Methyl Cellulose 2.0 gms of bupropion hydrobromide, 4.0 gms of hydroxylpropyl methyl cellulose are dissolved in 10 ml of dichloromethane and 10 ml of ethanol. The resulting clear solution was pumped through an ultrasonic atomizer in to a drying chamber using a Harvard syringe pump at a feed rate of 2.2 ml/min. The solvent was removed to provide the title compound.

The ultrasonic atomizer is commercially available from Sonotek, operated at a frequency of 60 Hz in top spray mode with an inlet gas temperature of 20° C. and an outlet gas temperature of 18° C.

The resulting amorphous bupropion hydrobromide solid dispersion with hydroxylpropyl methyl cellulose further compressed into tablets or filled in capsules.

Example 7

Preparation of an Amorphous Bupropion Hydrobromide Granulates with Hydroxyl Propyl Methyl Cellulose 2.0 gms of bupropion hydrobromide and 2.5 gms of hydroxylpropyl methyl cellulose are dissolved in 20 ml of water. The resulting solution was sprayed over the carrier bed consisting of lactose and microcrystalline cellulose, suspended in a fluid-bed granulator. The resultant title compound further dried and sieved.

Example 8

Composition for the preparation of bupropion hydrobromide tablet with amorphous bupropion hydrobromide solid dispersion with (2-Hydroxy propyl)-β-cyclodextrin.

| Ingredients | Weight % per tablet |
| --- | --- |
| Solid dispersion of bupropion hydrobromide with (2-Hydroxy propyl)-β-cyclodextrin of example 1 | 80-90% |
| Hydroxy propyl cellulose | 1.5-2.5% |
| Hydroxypropyl methyl cellulose | 5-10% |
| Polyvinylpyrrolidone | 2-5% |
| Silicon dioxide | 0.1-1% |
| Magnesium stearate | 0.1-1% |

Example 9

Composition for the preparation of bupropion hydrobromide tablet with amorphous bupropion hydrobromide granulates with povidone K25.

| Ingredients | Weight % per tablet |
| --- | --- |
| Amorphous bupropion hydrobromide granulates with povidone K25 of example 4 | 30% |
| Lactose monohydrate (Pharmatose DCL 11) | 41.5% |
| Microcrystalline cellulose | 20% |
| Crospovidone | 8% |
| Magnesium Stearate | 0.5% |

Example 10

Composition of the preparation of sustained release bupropion hydrobromide tablets with amorphous bupropion hydrobromide granulates with povidone K25.

| Ingredients | Mg/Tablet |
| --- | --- |
| Amorphous bupropion hydrobromide granulates with povidone K25 of example 4 | Equivalent to 174 Mg |
| Microcrystalline cellulose | 35.00 |
| Hydroxypropyl methyl cellulose (HPMC K 100 MCR) | 150.00 |
| Cysteine HCl | 20.00 |
| Ethyl Cellulose (Ethocel 20cps) | 10.0 |
| Talc | 3.00 |
| Magnesium Stearate | 8.00 |

Example 11

Composition of the preparation of sustained release bupropion hydrobromide tablets with amorphous bupropion hydrobromide inclusion complex with (2-Hydroxy propyl)-β-cyclodextrin.

| Ingredients | Weight % per tablet |
| --- | --- |
| Inclusion complex of bupropion hydrobromide with (2-Hydroxy propyl)-β-cyclodextrin | 30% |
| Microcrystalline cellulose | 26% |
| Hydroxypropyl methyl cellulose (K100MCR) | 30% |
| Cysteine Hcl | 3% |
| Purified water | q.s. |
| Ethyl cellulose (20cps) | 5% |
| Ethanol | q.s. |
| Talc | 1% |
| Magnesium Stearate | 2% |
| Film coating (Opadry white AMB) | 3.0% |

The invention claimed is:

1. A bupropion hydrobromide granulate comprising bupropion hydrobromide and at least one pharmaceutically acceptable carrier, wherein the bupropion hydrobromide exists in amorphous form.

2. The granulate of claim 1, wherein the granulate is in the form of a solid dispersion, an inclusion complex, or a spray granulate.

3. The granulate of claim 1, wherein the pharmaceutically acceptable carrier is selected from a group consisting of one or more of a povidone, meglumine, gum, ethyl cellulose, hydroxypropyl cellulose, hydroxypropyl methyl cellulose, hydroxypropyl ethyl cellulose, microcrystalline cellulose, cyclodextrin, gelatin, hypromellose phthalate, lactose, polyhydric alcohol, polyethylene glycol, polyethylene oxide, polyoxyalkylene derivative, methacrylic acid copolymer, polyvinyl alcohol, propylene glycol derivative, fatty acid, fatty alcohols, or esters of fatty acids.

4. A method of treatment of depressive disorders or smoking cessation, the method comprising preparing a pharmaceutical composition using amorphous bupropion hydrobromide granulate and administering an effective therapeutic dosage of the composition to patients in need thereof.

* * * * *